in(12) United States Patent
Yu et al.

(10) Patent No.: US 7,425,535 B2
(45) Date of Patent: *Sep. 16, 2008

(54) THERAPEUTIC PORE-FORMING PEPTIDES

(75) Inventors: Xianzhong Yu, Mauldin, SC (US); Thomas E. Wagner, Greer, SC (US)

(73) Assignee: GHC Research Development Corporation, Greenville, SC (US)

( * ) Notice: Subject to any disclaimer, the term of this patent is extended or adjusted under 35 U.S.C. 154(b) by 452 days.

This patent is subject to a terminal disclaimer.

(21) Appl. No.: 11/123,182

(22) Filed: May 6, 2005

(65) Prior Publication Data

US 2005/0267031 A1   Dec. 1, 2005

Related U.S. Application Data

(62) Division of application No. 09/851,422, filed on May 9, 2001, now Pat. No. 7,094,750.

(60) Provisional application No. 60/212,042, filed on Jun. 16, 2000, provisional application No. 60/203,063, filed on May 9, 2000.

(51) Int. Cl.
*A61K 38/16* (2006.01)
*A61K 38/33* (2006.01)
*A61K 45/00* (2006.01)
*C07K 14/195* (2006.01)
*C07K 14/435* (2006.01)

(52) U.S. Cl. ............................ 514/2; 514/12; 530/300; 530/324; 530/402; 530/820; 530/822; 530/823; 530/825

(58) Field of Classification Search ........................ None
See application file for complete search history.

(56) References Cited

U.S. PATENT DOCUMENTS

| 5,717,064 | A | 2/1998 | Julian et al. |
| 6,255,282 | B1 | 7/2001 | Jaynes |
| 6,265,540 | B1 | 7/2001 | Isaacs et al. |
| 2003/0138432 | A1 | 7/2003 | Glazier |

FOREIGN PATENT DOCUMENTS

| WO | PCT/97/33908 | 9/1997 |
| WO | WO 97/45544 | 12/1997 |
| WO | WO 03/092632 A2 | 11/2003 |

OTHER PUBLICATIONS

Takei et al (FEBS Letters, 1999, vol. 442, pp. 11-14).*
Rossjohn et al (Journal of Structural Biology, 1998, vol. 121, pp. 92-100).*
Blondelle et al., "Hemolytic and Antimicrobial Activities of the Twenty-Four Individual Omission Analogues of Melittin," *Biochemistry*, 1991, pp. 4671-4678, vol. 30, American Chemical Society.
Dempsey et al., "Contributioon of Proline-14 to the Structure and Actions of Melittin," *FEBS Letters*, 1991, pp. 240-244, vol. 281, No. 1,2, Elsevier Science Publishers B.V.
Leippe et al., "Cytolytic and Antibacterial Activity of Synthetic Peptides Derived from amoebapore, the Pore-Forming Peptide of *Entamoeba histolytica*," *Proc. Natl. Acad. Sci. USA*, 1994, pp. 2602-2606, vol. 91.
Andrä et al., "Shortened Amoebapore Analogs with Enhanced Antibacterial and Cytolytic Activity," *FEBS Letters*, 1996, pp. 96-100, vol. 385, Federation of European Biochemical Societies.
Shai et al., "Diastereomers of Cytolysins, a Novel Class of Potent Antibacterial Peptides," *Journal Biological Chemistry*, 1996, pp. 7305-7308, vol. 271 No. 13, The American Society for Biochemistry and Molecular Biology, Inc.
Werkmeister et al., "The Effect of Sequence Variations and Structure on the Cytolytic Activity of Melittin Peptides," *Biochimica et Biophysica Acta*, 1993, pp. 50-54, vol. 1157, Elsevier Science Publishers B.V.
Leippe et al., "Pore-Forming Peptide of Pathogenic *Entamoeba histolytica*," *Proc. Natl. Acad. Sci. USA*, 1991, pp. 7659-7663, vol. 88.
Horoszewicz et al., "LNCaP Model of Human Prostatic Carcinoma[1]," *Cancer Research*, 1983, pp. 1809-1818, vol. 43, No. 4, Dept. of Biological Resources, Roswell Park Memorial Inst. Buffalo, New York.
Pinto et al., "Prostate Specific Membrane Antigen, a Unique Glutamate Carboxypeptidase: A Review of Recent Findings," *The Prostate Journal*, 1999, pp. 15-26, vol. 1, No. 1, Blackwell Science, Inc.
Lopes et al., "Immunohistochemical and Pharmacokinetic Characterization of the Site-Specific Immunoconjugate CYT-356 Derived from Antiprostate Monoclonal Antibody," *Cancer Research*, 1990, pp. 6423-6429, vol. 50, American Association for Cancer Research.
Troyer et al., "Detection and Characterization of the Prostate-Specific Membrane Antigen (PSMA) in Tissue Extracts and Body Fluids," *Int. J. Cancer*, 1995, pp. 552-558, vol. 62, Wiley-Liss, Inc.
Wallrapp et al., "A Novel Transmembrane Serine Protease (TMPRSS3) Overexpressed in Pancreatice Cancer[1,2]," *Cancer Research*, 2000, pp. 2602-2606, vol. 60, No. 10, American Association for Cancer Research.
Wright et al., "Expression of Prostate-Specific membrane Antigen in Normal, Benign, and Malignant Prostate Tissues," *Urol. Oncol.*, 1995, pp. 18-28, vol. 1, Elsevier Science Inc., New York.
Prausnitz et al., "Electroporation of Mammalian Skin: A Mechanism to Enhance Transdermal Drug Delivery", Proc. Natl. Acad. Sci. USA, 1993, pp. 10504-10508, vol. 90, No. 22, Medical Sciences, NIH.
Wallace et al., "Stand and Deliver: Getting Peptide Drugs into the Body", Science, 1993, pp. 912-913, vol. 260, American Association for the Advancement of Science.
Andreu et al., "Solid-Phase Synthesis of Cecropin A and Related Peptides", Proc. Natl. Acad. Sci. USA, 1983, pp. 6475-6479, vol. 80, No. 21, Biochemistry, Biological Science.

(Continued)

*Primary Examiner*—Karen A. Canella
(74) *Attorney, Agent, or Firm*—Howrey LLP (57) ABSTRACT

A class of procytotoxic agents is characterized by a capability to kill with target cell-specificity. Such an aspect can be a pore-forming protein which has at least one lysine residue, modified by a peptide linkage to an amino acid residue, via the epsilon amino group. These agents are useful in treating cancer, especially prostate cancer.

15 Claims, 5 Drawing Sheets

OTHER PUBLICATIONS

Andreu et al., "N-Terminal Analogues of Cecropin A: Synthesis, Antibacterial Activity, and Confromational Properties", Biochemistry, 1985, pp. 1683-1688, vol. 24, No. 7, American Chemical Society.

Fink et al., "Design, Synthesis and Antibacterial Activity of Cecropin-Like Model Peptides", Int. J. Peptide Protein Res., 1989, pp. 412-421, vol. 33, No. 6, The Rockefeller University, New York, New York.

Fink et al., "The Chemical Synthesis of Cecropin D and an Analog with Enhanced Antibacterial Activity", J. of Biological Chemistry, 1989, pp. 6260-6267, vol. 264, No. 11, American Society for Biochemistry and Molecular Biology, Inc. Rockefeller University, New York.

Argiolas et al., "Bombolitins, a New Class of Mast Cell Degranulating Peptides from the Venom of the Bumblebee Megabombus Pennsylvanicus", J. of Biological Chemistry, 1985, pp. 1437-1444, vol. 260, No. 3, American Society of Biological Chemists, Inc.

Young et al., "Characterization of a Member Pore-Forming Protein From *Entamoeba histolytica*", J. Exp. Med. 1982, pp. 1677-1690, vol. 156, No. 6, The Rockefeller University Press.

Lynch et al., "An Ion-Channel Forming Protein Produced by *Entamoeba histolytica*", The EMBO Journal, 1982, pp. 801-804, vol. 1, No. 7, IRL Press Limited, Oxford, England.

Young et al., "Molecular Mechanisms of Cytotoxicity Mediated by *Entamoeba histolytica*: Characterization of a Pore-Forming Protein (PFP)", J. of Cellular Biochemistry, 1985, pp. 299-308, vol. 29 No. 4, Alan R. Liss, Inc.

Rosenberg et al., "Isolation, Characterization and Partial Purification of a Transferable Membrane Channel (Amoebapore) Produced by *Entamoeba histolytica*", Molecular and Biochemical Parasitology, 1989, pp. 237-248, vol. 33, No. 3, Elsevier Science Publishers B.V.

Jansson et al., "Coding of Hemolysins Within the Ribosomal RNA Repeat on a Plasmid in *Entamoeba histolytica*", Science, 1994, pp. 11440-11443, vol. 263, American Association for the Advancement of Science.

Woodle e tal., "Prolonged Systemic Delivery of Peptide Drugs by Long-Circulating Liposomes: Illustration with Vasopressin in the Brattleboro Rat", Pharmaceutical Research, 1992, vol. 9, No. 2, Plenum Press, New York.

Ch. Nagarjun Rao et al., "Role of amino groups in the biological activity of cytotoxin-3 from indian cobra venon," *Recent Adv. Toxinol. Res.*, (1992), 1:514-520 (XP001031413); summary p. 514, last paragraph—p. 515, paragraph 1, p. 517, paragraph 3—p. 518, paragraph 1; tables 1, 2.

S. Bourdenet et al., "The cytotoxicity of Pseudomonas exotoxin A, inactivated by modification of the cell-binding domain I, is restored when conjugated to an erythroid cell-specific targeting agent," *Cancer Letters*, (1990), 50(2):121-127 (XP001031414); summary p. 124, left-hand column, paragraph 2—p. 126, right-hand column, last paragraph.

Shinne-Ren Lin et al., "Chemical modification of amino groups in cardiotoxin III from Taiwan cobra (Naja naja atra) venom," *Biochemistry and Molecular Biology International*, (1993) 31(1):175-184 (XP001031369) p. 178, paragraph 1—p. 183, paragraph 1 summary.

E. Schroeder et al., "Hemolytic activity and action on the surface tension of aequeous solutions of synthetic melittins," *Experientia* (1971) 27(7):764-765 (XP001031342).

Jörg Andrä et al., "Shortened amoebapore analogs with enhanced antibacterial and cytolytic activity," *FEBS Letters* (1996) 385:96-100 (XP002182888) abstract, p. 97, right-hand column, paragraph 2—p. 100, right hand column, paragraph 1.

Liu et al., (1979), *Endrocrinology*, vol. 104, pp. 962-966, abstract only.

Fernandez-Lopez et al., "Antibacterial Agents Based on the Cyclic D,L-α-Peptide Architecture", Letters of Nature, 2001, pp. 452-455, vol. 412.

Huse et al., "Generation of a Large Combinatorial Library of the Immunoglobulin Repertoire in Phage Lambda", Science, 1989, pp. 1275-1281, vol. 246, Research Article.

Coombs et al., "Substrate Specificity of Prostate-Specific Antigen (PSA)", Chemistry & Biology, 1998, pp. 475-488, vol. 5, No. 9, Research Paper.

\* cited by examiner

MELLITIN-GAMMA-GLUTAMINE CYTOTOXICITY TOWARDS TUMOR CELL LINES

Legend:
- □ LNCaP-FCG(H)
- △ SK-OV-3(H)
- ✕ B16(M)
- ✱ HeLa(H)
- + LLC1(M)
- — DU-145(H)

(H) = HUMAN
(M) = MURINE

FIG. 5

THERAPEUTIC PORE-FORMING PEPTIDES

FIELD OF THE INVENTION

This invention relates to methods and compositions for treating cancer. Specifically, the invention relates to the use of a procytotoxin that can be converted to a cytotoxin in a tumor-cell specific manner, such that the tumor cell is destroyed by the activated cytotoxin.

BACKGROUND OF THE INVENTION

Present methods for tumor treatment, especially cancer treatment, remain sub-optimal and often are accompanied by severe complications. In fact, virtually all of the known therapies have serious adverse side effects, most often caused by the lack of specificity and thoroughness in the destruction or removal of tumor or cancer cells.

For example, surgery, a common procedure for removing cancerous cells from a patient, often is incomplete, and it disfigures the patient or interferes with normal bodily functions. Similarly, chemotherapy and radiation treatment often indiscriminately destroys normal cells, causing unwanted side-effects, while leaving many cancer cells unaffected. Chemotherapeutic agents, especially antimetabolites, while effective to varying degrees against cancer cells that are continuously undergoing or preparing for mitosis, are not effective against cancer cells that are in the resting ($G_0$) stage.

Cancer treatment is most effective when cancer cells can be eliminated as completely as possible from the patient's body. To achieve this goal, continuous or consecutive dosages are administered to the patient. Because most available chemotherapeutic agents are also toxic to normal cells, the dose of cytotoxic drug is adjusted to the limits of tolerance to achieve the maximum destruction of malignant cells, and the interval between doses must be such that the rate of tumor re-growth does not exceed tumor killing. Accordingly, in order to achieve increased efficiency, the chemotherapeutic agents should have high target-cell specificity and high target-cell toxicity or potency.

Prostate cancer is the most common form of cancer among males, with an estimated incidence of 30% in men over the age of 50. Overwhelming clinical evidence shows that human prostate cancer has the propensity to metastasize to bone, and the disease appears to progress inevitably from androgen-dependent to androgen-refractory status, leading to increased patient mortality. This prevalent disease is currently the second leading cause of cancer death among men and prostate cancer metastasis is estimated to claim the lives of over 30,000 Americans each year. In spite of considerable research into therapies for cancer, currently available treatment methods are ineffective in a significant percentage of cases.

Accordingly, there is a need for improved cancer treatment and more methods that are not dependent upon the cell cycle of the cancer cell. Particularly, there is a need for improved treatment methods for prostate cancer. The present invention fulfills these needs and further provides other related advantages.

SUMMARY OF THE INVENTION

It therefore is an object of the present invention to overcome some or all of the aforementioned deficiencies in conventional therapies, especially with regard to treating prostate cancer. To this end, a procytotoxin is provided which typically is made up of a cytotoxic peptide having at least one lysine residue. In general, at least one lysine of the cytotoxin is bound through its ε-amino group, via an ε-γ peptide bond, to the γ-carboxyl group of a glutamic acid residue. In different embodiments, one, two, or more additional glutamate residues are bound to the one attached to the lysine. Generally preferred cytotoxins include Ae I, cytolysin of sea anemone, aerolysin, amatoxin, amoebapore, amoebapore homolog from *Entamoeba dispar*, brevinin-1E, brevinin-2E, barbatolysin, cytolysin of *Enterococcus faecalis*, delta hemolysin, diphtheria toxin, EI Tor cytolysin of *Vibrio cholerae*, equinatoxin, enterotoxin of *Aeromonas hydrophila*, esculentin, granulysin, haemolysin of *Vibrio parahaemolyticus*, intermedilysin of *Streptococcus intermedius*, the lentivirus lytic peptide, leukotoxin of *Actinobacillus actinomycetemcomitans*, magainin, melittin, membrane-associated lymphotoxin, Met-enkephalin, neokyotorphin, neokyotorphin fragment 1, neokyotorphin fragment 2, neokyotorphin fragment 3, neokyotorphin fragment 4, NK-lysin, paradaxin, perforin, perfringolysin O, theta-toxin, of *Clostridium perfringens*, phallolysin, phallotoxin, streptolysin, and analogs and derivative thereof.

Particularly preferred procytotoxins have the following structures: (1) Gly-Phe-Ile-Ala-Thr-Leu-Cys-Thr-Lys(R)-Val-Leu-Asp-Phe-Gly-Ile-Asp-Lys(R)-Leu-Ile-Gln-Leu-Ile-Glu-Asp-Lys(R), and (2) Gly-Ile-Gly-Ala-Val-Leu-Lys(R)-Val-Leu-Thr-Thr-Gly-Leu-Pro-Ala-Leu-Ile-Ser-Trp-Ile-Lys(R)-Arg-Lys(R)-Arg-Gln-Gln, wherein R is independently selected from the group consisting of the unmodified ε-amino group of the adjacent lysine residue, [ε-γ]-Glu, [ε-γ]-Glu-[α-γ]-(Glu)$_{1-3}$, [ε-α]-(Phe)$_{1-3}$, [ε-α]-(Tyr)$_{1-3}$, [ε-α]-(Trp)$_{1-3}$, [ε-α]-(Lys)$_{1-3}$ and [ε-α]-(Arg)$_{1-3}$, wherein [ε-γ] represents a peptide bond between the epsilon amino group of lysine and the gamma carboxyl group of the adjacent glutamate, [α-γ] represents a peptide bond between the alpha amino group of the first glutamate and the gamma carboxyl group of the second glutamate, [ε-α] represents a peptide bond between the epsilon amino acid of lysine and the alpha carboxyl group of the indicated amino acid and the subscript indicates that additional numbers of the designated amino acid can be linked to the first via conventional peptide bonds.

Also provided, in achieving this objective of the invention, are pharmaceutical compositions that, in general, contain an inventive procytotoxin and a pharmaceutically acceptable excipient.

Further, methodology is provided for destroying a target cell selectively. This approach typically entails bringing an inventive procytotoxin into contact with a target cell, which generally will have a cell-surface glutamate carboxypeptidase, like prostate specific membrane antigen. Thus, prostate cancer cells are preferred target cells.

Further to the same object, a method for treating prostate cancer is provided. In general, the method comprises administering to a patient in need, a pharmaceutical composition containing procytotoxin according to the invention. The preferred route of administration is parenteral. Preferred compositions contain procytotoxins based on amoebapore, a melittin or a cytolytic peptide derived therefrom.

DETAILED DESCRIPTION OF THE PREFERRED EMBODIMENTS

The present invention provides a pharmaceutical composition and a method for selectively destroying a target cell, like a cancer cell. The pharmaceutical composition comprises a procytotoxin that can be activated in a target cell-specific manner, thereby killing, destroying or eliminating the target cell.

A procytotoxin according to the present invention is a compound that is not itself cytotoxic but may be converted into a cytotoxin. A cytotoxin is a substance that is harmful, destructive or deadly to a cell. A preferred cytotoxin according to the present invention kills or otherwise eliminates the target cell from a patient with high potency.

The pharmaceutical composition according to the instant invention generally does not affect nontarget cells. In a preferred embodiment, target cell-specific activation of the procytotoxin occurs only at or near the target cells. When the pharmaceutical composition is used for treating cancer cells, the procytotoxin remains in an inactive state, thus is nontoxic, until it reaches the cancer site. In the case of cancer treatment, the procytotoxin is activated at the surface of the cancer cells and, thereby, it achieves high specificity in the destruction of target cells versus normal cells. Once the procytotoxin is activated in a target cell-specific manner, the high potency of the cytotoxin ensures that the pharmaceutical composition achieves a thorough destruction of the target cells.

Cytotoxic Peptides

According to one embodiment of the invention, a procytotoxin is a cytotoxic peptide that is rendered non-toxic by modification of its molecular structure, as detailed below. Many naturally occurring and synthetic cytotoxic peptides are known in the art. Some are useful as therapeutic agents against pathogenic bacteria and other classes of microorganisms; they may be isolated from insects, frogs and other animals. Specific examples include alamethicins, attacins, bactenecins, cecropins (see Table 1 the amino acid sequences of cecropins A, B and C), CytA and CytB of *Bacillus thurigiensis*, defensins, enterocin L50 (pediocin L50), lantibiotics, magainins, PGLa, protegrins, sapecin, and sarcotoxin.

A preferred cytotoxic peptide is a cytolytic peptide. Cytolytic peptides, also known as channel-forming peptides, typically disrupt cell membranes, causing cell lysis and death upon contact. Many naturally occurring cytolytic peptides from microorganisms, from insects and from higher animals are generally known. They often are called hemolysins because they lyse red blood cells as well as other eukaryotic cells. These toxins include Ae I and other cytolysins of sea anemone, aerolysin, amatoxins, amoebapores, amoebapore homologs from *Entamoeba dispar*, brevinin-1E, brevinin-2E, barbatolysin, cytolysin of *Enterococcus faecalis*, delta hemolysin, diphtheria toxin, El Tor cytolysin of *Vibrio cholerae*, equinatoxins, enterotoxin of *Aeromonas hydrophila*, esculentin, granulysin, haemolysin of *Vibrio parahaemolyticus*, intermedilysin of *Streptococcus intermedius*, the lentivirus lytic peptide, leukotoxin of *Actinobacillus actinomycetemcomitans*, magainin, melittin, membrane-associated lymphotoxin, Met-enkephalin, neokyotorphin and neokyotorphin fragments (1-4), NK-lysin, paradaxins, perforin (especially its amino terminus), perfringolysin O (PFO or theta-toxin) of *Clostridium perfringens*, phallolysins and phallotoxins, and streptolysins. Some hemolysins like melittin are also known to kill bacteria.

Many cytolytic peptides are pore-forming toxins, belonging to a group of cytotoxins that associate with cell membranes, nonspecifically or to specific receptors, and form transmembrane pores of discrete size. Most toxic pore-forming peptides employ common features for their cell lysis activity. For example, a great number of these toxins lyse cells through a "barrel-stave" mechanism, in which monomers of the toxin bind to and insert into the target membrane and then aggregate like barrel staves surrounding a central, water filled pore. This pore causes rapid and irreversible electrolyte imbalance of the target cell leading to its destruction.

Most pore-forming peptides that act on both mammalian and bacterial cells require an amphipathic alpha-helical structure and a net positive charge for their cytolytic activity. A strong electrostatic interaction between the cationic portion of the peptide and the lipid headgroups weakens the membrane, facilitating insertion of the hydrophobic alpha-helical peptides. Accordingly, a particularly preferred cytotoxic peptide according to the invention is a cytolytic, linear α-helical peptide. Generally these cytotoxic peptides, in their native form, will have a net positive charge, which contributes to their cytolytic activity.

According to a preferred embodiment of the invention, the cytolytic peptide is melittin or an analog or derivative thereof. Melittin is isolated from bee venom and is a 26 amino acid amphiphilic alpha-helix (Blondelle et al., (1991) Biochemistry 30: 4671-4678; Dempsey et al., (1991) FEBS Lett. 281: 240-244.) The amino acid sequence of melittin is shown in Table 1. Residues 1-20 are predominantly hydrophobic and residues 21 to 26 are hydrophilic and basic. Melittin has antibiotic activity, but in mammals it is lytic for leukocytes, red blood cells and a wide variety of other cells. Compounds similar to melittin, which are also within the scope of the invention, include bombolitin from bumblebee venom (17 amino acid amphiphilic alpha-helix), mastoparan from wasp venom (14 amino acid amphiphilic alpha-helix) and crabrolin from hornet venom (13 amino acid amphiphilic alpha-helix) Argiolas A. and Pisano J. J., 1985, J. Biol. Chem. 260, 1437-1444.).

TABLE 1

Amino Acid Sequence of Selected Cytolytic Peptides

Amoebapore Helix 3 (*Entamoeba histolytica*)
$NH_2$-Gly-Phe-Ile-Ala-Thr-Leu-Cys-Thr-Lys-Val-Leu-Asp-Phe-Gly-Ile-Asp-Lys-Leu-Ile-Gln-Leu-Ile-Glu-Asp-Lys-$CONH_2$ Cecropin A (*Antheria pernyi*)
$NH_2$-Lys-Trp-Lys-Leu-Phe-Lys-Lys-Ile-Glu-Lys-Val-Gly-Gln-Asn-Ile-Arg-Asp-Gly-Ile-Ile-Lys-Ala-Gly-Pro-Ala-Val-Ala-Val-Val-Gly-Gln-Ala-Thr-Gln-Ile-Ala-Lys-COOH

TABLE 1-continued

Amino Acid Sequence of Selected Cytolytic Peptides

Cecropin B (*Antheria pernyi*)
NH$_2$-Lys-Trp-Lys-Ile-Phe-Lys-Lys-Ile-Glu-Lys-Val-
Gly-Arg-Asn-Ile-Arg-Asn-Gly-Ile-Ile-Lys-Ala-Gly-
Pro-Ala-Val-Ala-Val-Leu-Gly-Glu-Ala-Lys-Ala-Leu-
COOH Cecropin D (*Antheria pernyi*)
NH$_2$-Trp-Asn-Pro-Phe-Lys-Glu-Leu-Glu-Lys-Val-Gly-
Gln-Arg-Val-Arg-Asp-Ala-Val-Ile-Ser-Ala-Gly-Pro-
Ala-Val-Ala-Thr-Val-Ala-Gln-Ala-Thr-Ala-Leu-Ala-
Lys-COOH Melittin (*Apis mellifera*)
NH$_2$-Gly-Ile-Gly-Ala-Val-Leu-Lys-Val-Leu-Thr-Thr-
Gly-Leu-Pro-Ala-Leu-Ile-Ser-Trp-Ile-Lys-Arg-Lys-
Arg-Gln-Gln-COOH A particularly preferred pore-forming peptide, according to the instant invention, is amoebapore, a 77-residue pore-forming peptide from the amoebae *Entamoeba histolytica* (Young et al., (1982) J. Exp. Med. 156: 1677; Lynch et al., (1982) EMBO J. 7: 801; Young & Cohn, (1985) J. Cell Biol. 29: 299; Rosenberg et al., (1989) Molec. Biochem. Parasit. 33: 237; Jansson et al., (1994) Science 263: 1440). It has four alpha helices, from amino acids approximately 1-21, 25-36, 40-63 and 67-77, conventionally called helices 1, 2, 3, and 4, respectively.

Three isoforms of amoebapore are known: amoebapore A, B and C, respectively. This peptide is stabilized by three disulfide bonds and contains four mostly amphipathic alpha-helical structures. The third amphipathic helical structure (helix 3) retains the cytolytic activity similar to the wild type peptide. A synthetic peptide based on the sequence of its third amphipathic alpha helix have recently been shown to have cytolytic activity for nucleated cells at high concentrations (10-100 μM) (Leippe et al., (1994) Proc. Natl. Acad. Sci. USA 91: 2602). This peptide, depicted above in Table 1, represents a preferred cytolytic peptide.

Some representative pore-forming cytolytic peptides are selected from the group consisting of Ae I, cytolysin of sea anemone, aerolysin, amatoxin, amoebapore, amoebapore homolog from *Entamoeba dispar*, brevinin-1E, brevinin-2E, barbatolysin, cytolysin of *Enterococcus faecalis*, delta hemolysin, diphtheria toxin, El Tor cytolysin of *Vibrio cholerae*, equinatoxin, enterotoxin of *Aeromonas hydrophila*, esculentin, granulysin, haemolysin of *Vibrio parahaemolyticus*, intermedilysin of *Streptococcus intermedius*, the lentivirus lytic peptide, leukotoxin of *Actinobacillus actinomycetemcomitans*, magainin, melittin, membrane-associated lymphotoxin, Met-enkephalin, neokyotorphin, neokyotorphin fragment 1, neokyotorphin fragment 2, neokyotorphin fragment 3, neokyotorphin fragment 4, NK-lysin, paradaxin, perforin, perfringolysin O, theta-toxin, of *Clostridium perfringens*, phallolysin, phallotoxin, and streptolysin.

It is readily recognized that the above described cytolytic peptides may be modified or derivatized to produce analogs and derivatives which retain, or even exhibit enhanced, cytolytic activities. For example, Andra et al. disclose that shortened amoebapore analogs have enhanced antibacterial and cytolytic activities (FEBS Letters, 385 (1996), pp. 96-100, incorporated herein by reference in its entirety).

In designing such analogs or derivatives, the artisan will be informed by the foregoing discussion relating to the amphipathic alpha-helical structure and net positive charge that are implicated in the cytolytic activity. Thus, a skilled artisan is able to design amoebapore analogs, i.e., non-native forms never before known in nature, based on the observed homologies and known structure and properties of the native protein, to be used as a cytolytic peptide in accordance with the instant invention.

Modification and derivatization according to the instant invention include, but are not limited to, substitutions, additions or deletions that provide for functionally equivalent molecules. (Function may be assessed in accord with the working examples presented below.) Analogs and derivatives may also be made via modifications of side chains of amino acid residues of the cytotoxic peptides, preferably, with enhanced or increased functional activity relative to the native protein or polypeptide.

For example, analogs and derivatives of an amoebapore or other cytolytic peptides include, but are not limited to, those containing, as a primary amino acid sequence, all or part of the amino acid sequence the native peptide, such as with altered sequences in which functionally equivalent amino acid residues are substituted for residues within the sequence resulting in a conservative amino acid substitution. For example, one or more amino acid residues within the sequence can be substituted by another amino acid of a similar polarity, which acts as a functional equivalent, resulting in a silent alteration. Substitutes for an amino acid within the sequence may be selected from other members of the class to which the amino acid belongs. For example, nonpolar (hydrophobic) amino acids include alanine, leucine, isoleucine, valine, proline, phenylalanine, tryptophan and methionine. Polar neutral amino acids include glycine, serine, threonine, cysteine, tyrosine, asparagine, and glutamine. Positively charged (basic) amino acids include arginine, lysine and histidine. Negatively charged (acidic) amino acids include aspartic acid and glutamic acid. Because the terminal positive charges are thought to be involved in the cytolytic activity of the peptide, addition or substitution of a positively charged amino acid at the C-terminus is particularly contemplated to enhance its cytolytic potency.

Dimerization, truncation, diasteroisomers (D-amino acid-incorporated analogs) (Shai et al., (1996) J. Biol. Chem. 271-7305-7308), and combinations thereof may also be employed for producing derivatives and analogs of pore-forming peptides. For example, Werkmeister et al. (1993), Biochim. Biophys. Acta 1157: 50-54, discloses the effect of sequence and structural variations on the cytolytic activity of melittin, and is hereby incorporated by reference in its entirety.

The cytolytic peptides of the invention will normally contain from about 15 to about 40 amino acid residues. It is apparent to one skilled in the art that active low molecular weight peptides containing less than about 40 amino acids (or even less than about 30) are normally not difficult to synthesize chemically, while peptides with more than about 40 amino acids are relatively difficult to synthesize in pure form by chemical methods, and may be best prepared by fermentation or by recombinant DNA procedures from the appropriate genetic coding sequence. A particular advantage of the useful peptides of this invention is that they are readily synthesized by solid phase methods and a variety of combinations are possible to achieve specifically required results. An advantage of the use of solid phase techniques is that the product can be directly synthesized with the C-terminus amidated or otherwise blocked, which is beneficial in forming the procytotoxins of the invention. For example, one procytotoxin requires formation of γ-glutamate peptide bonds which are readily produced by such chemical synthesis.

A particularly preferred cytotoxin is an amoebapore derivative: NH²-Gly-Phe-Ile-Ala-Thr-Leu-Cys-Thr-Lys-Val-Leu-Asp-Phe-Gly-Ile-Asp-Lys-Leu-Ile-Gln-Leu-Ile-Glu-Asp-Lys-CONH$_2$ Producing Procytotoxins In order to enhance its therapeutic usefulness, a cytotoxin is modified according to the invention to render it to a non-toxic protoxin form. Numerous methods of modifications are available, the applicability of which will depend on the structural characteristics of the cytotoxin. A peptide, for example, may be added to either the N-terminus and/or the C-terminus of the cytotoxic peptide, such that the cytotoxic peptide is rendered non-toxic.

A preferred method is to disrupt the alpha-helical structure of the cytotoxin, generally by sterically preventing the structure from forming and/or eliminating/neutralizing the positive charge of the pore-forming peptide. Because this charge is involved in its cytolytic activity, such neutralization renders the peptide non-toxic. It is envisioned that even a partial neutralization of this positive charge will be effective. Moreover, it also will be understood that steric determinants also may be important, in addition to or instead of, charge determinants. Thus, even if no neutralization is accomplished, some of the modifications below will result in steric alterations which will inactivate the toxin to create the protoxin.

The inventors have recognized that a common feature of the aforementioned cytotoxins is the presence of one or more lysine residues. Accordingly, a preferred means of preparing a protoxin is to modify one or more of these lysine residues. Thus, for example, by addition via a peptide bond of a negatively charged amino acid to the epsilon amino group of lysine, charge neutralization and/or steric mechanisms are invoked to maintain the toxin as a protoxin. Of course, where a native molecule lacks a lysine, it may be added and modified, which still is expected to invoke the steric inhibition of toxin formation. Generally, the amino acid added to the epsilon amino group using a peptide linkage will be the target of a membrane-associated protease. An increasing number of such enzymes are being identified which are correlated with neoplastic or preneoplastic states. Thus, they are convenient targets for therapy.

In one aspect protoxin formation is accomplished via the conversion of an epsilon amino group of a lysine residue to a neutral peptide linkage and/or the addition of one or more negatively charged amino acid residues at or near this position. A preferred negatively charged amino acid is glutamate. In a particularly preferred embodiment the epsilon amino group of lysine is bound by a peptide linkage to the gamma carboxyl group of glutamate. The resultant free alpha carboxyl group in such a case is free to neutralize additional adjacent positively charged amino acids, like arginine, which is expected to further repress the activity of the cytotoxin. In some embodiments it is envisioned that more than one glutamic acid (poly-α-γ-glutamate) is added to a lysine. Thus, a peptide lysine is bound via an ε-γ linkage to a glutamate and that glutamate is bound to a second glutamate via an α-γ peptide bond. The second glutamate may be bound to a third, and so on.

It will be apparent to the artisan, therefore, that a more general aspect of the invention entails adding any amino acid to partially or wholly neutralize the subject positive charge, or otherwise to sterically inhibit formation of the toxin. For example, where a lysine residue is present, as described above, any amino acid may be linked to the epsilon amino group, via a linkage with the alpha carboxyl group of the added amino acid. In general, a salient feature is the ability of the added amino acid to be proteolytically cleaved in order to form toxin from protoxin. Thus, in the case of chymotrypsin-like activity, the bulky hydrophobic amino acids, like tyrosine, phenylalanine and tryptophan may be employed. In a case where steric considerations alone are sufficient to inactivate the toxin, positively charged amino acids like arginine and lysine may be employed to invoke trypsin-like activity. Other examples also are apparent based on the artisan's knowledge of protease specificities.

Particularly preferred procytotoxins include amoebapore, its analogs and its derivatives that contains one or more γ-linked glutamate residues linked via a peptide bond to the epsilon amino group of at least one lysine, preferably the C-terminal-most lysine (hereinafter "γ-glutamate-masked amoebapore analog"). A particularly preferred procytotoxin has the following structure: Gly-Phe-Ile-Ala-Thr-Leu-Cys-Thr-Lys-Val-Leu-Asp -Phe-Gly-Ile-Asp-Lys-Leu-Ile-Gln-Leu-Ile-Glu-Asp-Lys-[ε-γ]-Glu-[α-γ]-Glu, wherein [ε-γ] represents a peptide bond between the epsilon amino group of lysine and the gamma carboxyl group of the adjacent glutamate and [α-γ]represents a peptide bond between the alpha amino group of the first glutamate and the gamma carboxyl group of the second glutamate.

In addition, amoebopore and other cytotoxic peptides can be modified with other amino acids. One such exemplary protoxin has the following structure: Gly-Phe-Ile-Ala-Thr-Leu-Cys-Thr-Lys-Val-Leu-Asp-Phe-Gly-Ile-Asp-Lys-Leu-Ile-Gln-Leu-Ile-Glu-Asp-Lys-[ε-α]-Phe, wherein [ε-α] represents a peptide bond between the epsilon amino group of lysine and the alpha carboxyl group of the adjacent phenylalanine. Another exemplary protoxin that can be activated by chymotrypsin-like activity has the following structure: Gly-Phe-Ile-Ala-Thr-Leu-Cys-Thr-Lys-Val-Leu-Asp-Phe-Gly-Ile-Asp-Lys([ε-α]-Phe)-Leu-Ile-Gln-Leu-Ile-Glu-Asp-Lys-[ε-α]-Phe, using the same nomenclature and where Lys([ε-α]-Phe)-Leu represents a linkage between the epsilon amino group of lysine and the alpha carboxy group of phenylalanine, and a standard peptide linkage between lysine and phenlyalanine. Of course, the phenylalanine may be replaced with other amino acids, such as tyrosine and tryptophan in the case of chymotrypsin-like activity. In some instances, in order to invoke trypsin-like activity, it may be beneficial to utilize positively charged amino acids, like arginine and lysine, instead of phenylalanine.

Other particularly preferred procytotoxins include melittin, its analogs and its derivatives that contain at least one γ-linked glutamate residue linked via a peptide bond to the epsilon amino group of a lysine (hereinafter "γ-glutamate-masked melittin analog"). As indicated in Table 1, melittin has two lysines and two adjacent arginines near its C-terminus. When one of the lysines is so masked, it is expected that the free alpha carboxyl group would act to neutralize the adjacent arginine, further contributing to the inhibition of the toxic activity of melittin. A particularly preferred procytotoxin has the following structure: Gly-Ile-Gly-Ala-Val-Leu -Lys-Val-Leu-Thr-Thr-Gly-Leu-Pro-Ala-Leu-Ile-Ser-Trp-Ile-Lys([ε-γ]-Glu)-Arg-Lys([ε-γ]-Glu)-Arg-Gln-Gln, wherein -Lys-([ε-γ]-Glu)-Arg-represents a peptide bond between the epsilon amino group of lysine and the gamma carboxyl group of the adjacent glutamate and a standard peptide bond between the lysine and arginine residues. Of course, -Lys-([ε-γ]-Glu)-Arg- can be replaced, for example, by -Lys([ε-α]-Phe)-Leu-, as detailed above, and phenylalanine can be replaced by other amino acids like tyrosine and tryptophan to invoke chymotrypsin-like activity. In some instances, when trypsin-like activity is being invoked, it may be beneficial to utilize positively charged amino acids, like arginine and lysine, instead of phenylalanine in this latter example.

With regard to the terminology used herein, the artisan will recognize that a "standard" peptide bond is formed between the alpha carboxyl group of one amino acid with the alpha amino group of the next amino acid in the peptide chain and that peptide sequences are read from their amino-terminal end to their carboxyl-terminal end. For clarification, the following structures of glutamic acid and lysine are presented with the various groups named according to which carbon of the amino acid backbone they attach:

$$\underset{\alpha\text{ amino}}{\overset{\alpha\text{ carboxyl}}{\underset{^+H_3N}{^-O_2C}}}\underset{\alpha}{\diagdown}\underset{\beta}{\diagup}\underset{\gamma}{\diagdown}\underset{\gamma\text{ carboxyl}}{CO_2^-}$$

Glutamic Acid $$\underset{\alpha\text{ amino}}{\overset{\alpha\text{ carboxyl}}{\underset{^+H_3N}{^-O_2C}}}\underset{\alpha}{\diagdown}\underset{\beta}{\diagup}\underset{\gamma}{\diagdown}\underset{\delta}{\diagup}\underset{\epsilon}{\diagdown}\underset{\epsilon\text{ amino}}{NH_3^+}$$

Lysine

In sum, a set of particularly preferred procytotoxins have the following structures: (1) Gly-Phe-Ile-Ala-Thr-Leu-Cys-Thr-Lys(R)-Val-Leu-Asp-Phe-Gly-Ile-Asp-Lys(R)-Leu-Ile-Gln-Leu-Ile-Glu-Asp-Lys(R), and (2) Gly-Ile-Gly-Ala-Val-Leu-Lys(R)-Val-Leu-Thr-Thr-Gly-Leu-Pro-Ala-Leu-Ile-Ser-Trp-Ile-Lys(R)-Arg-Lys(R)-Arg-Gln-Gln, wherein R is independently selected from the group consisting of the ε-amino group of the adjacent lysine residue, [ε-γ]-Glu, [ε-γ]-Glu-[α-γ]-(Glu)$_{1-3}$, [ε-α]-(Phe)$_{1-3}$, [ε-α]-(Tyr)$_{1-3}$, [ε-α]-(Trp)$_{1-3}$, [ε-α]-(Lys)$_{1-3}$ and [ε-α]-(Arg)$_{1-3}$, wherein [ε-γ] represents a peptide bond between the epsilon amino group of lysine and the gamma carboxyl group of the adjacent glutamate, [α-γ] represents a peptide bond between the alpha amino group of the first glutamate and the gamma carboxyl group of the second glutamate, [ε-α] represents a peptide bond between the epsilon amino acid of lysine and the alpha carboxyl group of the indicated amino acid and the subscript indicates that additional numbers of the designated amino acid can be linked to the first via conventional peptide bonds. With regard to the subscripted numbers, it is understood that larger numbers of amino acids are possible, e.g., 4, 5, 6, etc., but 1, 2, and 3 are anticipated to be optimal.

While not wishing to be bound by any theory, the inventors recognize the importance of the positive charges for the mode of action of the amoebapore and related cytotoxic molecules, and believe that the glutamate residues added according to the invention neutralize and reverse the polarity of these positive charges of a cytolytic peptide or its analog or derivative, thus negating its cell-lysing activities. In the case of other amino acids, they may function by a partial neutralization. Of course, steric determinants also are believed to be important in maintaining the toxins in protoxin form in many, if not all cases.

The procytotoxic peptides of this invention may be chemically synthesized by standard solid phase procedures using the protection, deprotection and cleavage techniques and reagents appropriate to each specific amino acid or peptide. A combination of manual and automated (e.g., APPLIED BIO-SYSTEM.®™ 430A) solid phase techniques can be used to synthesize the novel peptides of this invention. For background on solid phase techniques, reference is made to Andreu et al., (1983) Proc. Natl. Acad. Sci USA 80: 6475-6479; Andreu et al., (1985) Biochemistry 24: 1683-1688; Fink et al. (June 1989) Int. J. Peptide Protein Res. 33: 412-421; Fink et al., (1989) J. Biol. Chem. 264: 6260-6267; each of which is incorporated herein by reference.

The in vivo stability of the procytotoxin of the invention can be improved by adding a D-amino acid to the N- or C-terminus, whichever does not have a γ-linked glutamic acid residue. (Of course, some in vivo instability would be advantageous because it would decrease the chance of possible adverse side effects that might arise once the procytotoxin is converted to cytotoxin.) This procedure is particularly useful with products of the invention which are employed under conditions, parenteral or oral, where they will be subject to hydrolysis by naturally occurring enzymes before they perform their desired physiological function.

Pharmaceutical Compositions

A further aspect of the present invention provides pharmaceutical compositions which comprise one or more procytotoxins of the invention and a pharmaceutically acceptable carrier or excipient.

While a procytotoxic peptide of the present invention can be administered, alone, to a patient, it is preferable to present the peptide as part of a pharmaceutical formulation. Pharmaceutically acceptable carriers typically include carriers known to those skilled in the art, including pharmaceutical adjuvants. Generally, these pharmaceutically acceptable carriers will include water, saline, buffers, and other compounds described, e.g., in the MERCK INDEX, Merck & Co., Rahway, N.J. See also Bioreversible Carriers in Drug Design, Theory and Application, Roche (ed.), Pergamon Press, (1987). These formulations typically comprise the pharmacological agent (i.e., the procytotoxin) in a therapeutically or pharmaceutically effective dose together with one or more pharmaceutically or therapeutically acceptable carriers and optionally other therapeutic ingredients. Various considerations are described, e.g., in Gilman et al. (eds) (1990) Goodman and Gilman's: The Pharmacological Bases of Therapeutics, 8th Ed., Pergamon Press; Novel Drug Delivery Systems, 2nd Ed., Norris (ed.) Marcel Dekker Inc. (1989), and Remington's Pharmaceutical Sciences, the full disclosures of which are incorporated herein by reference.

The compositions may be formulated in any pharmaceutical form appropriate for the desired route of administration. Examples of such compositions include solid compositions for oral administration such as tablets, capsules, pills, powders and granules which may be enteric coated or otherwise protected from hydrolysis, especially enzymatic hydrolysis, liquid compositions for oral administration such as solutions, suspensions, syrups or elixirs and preparations for parenteral administration such as sterile solutions, suspensions or emulsions. The compositions may also be manufactured in the form of sterile solid compositions which can be dissolved in sterile water, physiological saline or some other sterile injectable medium immediately before use.

Since the procytotoxins of the invention are amphoteric they may be utilized as free bases, as acid addition salts or as metal salts. The salts must, of course, be pharmaceutically acceptable, and these will include metal salts particularly alkali and alkaline earth metal salts, suitably potassium or sodium salts. A wide variety of pharmaceutically acceptable acid addition salts are available. These include those prepared from both organic and inorganic acids, preferably mineral acids. Typical acids which may be mentioned by way of example include citric, succinic, lactic, hydrochloric and hydrobromic acids. Such products are readily prepared by procedures well known to one skilled in the art.

In all such compositions, the cytolytic peptides will normally be the principal physiologically active ingredient. The inventive peptides may be formulated, however, with additional pharmacological agents for combination therapies. When used in treating cancer, for example, they may be formulated with compatible conventional chemotherapeutic agents.

Methods for administration are also discussed in Gilman et al. (eds) (1990) and Norris (ed.), supra. In particular, the pharmaceutical composition of the invention may be administered intravenously, subcutaneously, orally, transdermally, such as in the method of (Prausnitz, M R, Bose, V G, Langer, R, Weaver, J C: Electroporation of Mammalian skin: a mechanism to enhance transdermal drug delivery. Proc. Nat'l. Acad. Sci. U.S.A., 90:10504-10508 (1993); and Wallace, B M, Lasker, J S: Stand and Deliver: getting peptide drugs into the body. Science 260:912-912 (1992). Liposomes may also be used to administer the procytotoxin of the invention (see Woodle, M C, Storm, G, Newman, M S, Jekot, J J, Collins, L R, Martin, F J, Szoka F C: Prolonged systemic delivery of peptide drugs by long circulating liposomes: illustration with vasopressin in the Brattleboro rat. Pharmaceut. Res. 9:260-265 (1992).

Methods of Treatment

The peptide protoxin of the present invention typically is converted, and thereby activated, into a cytotoxic peptide in a target cell-specific manner by an activity associated with the target cell. In other words, the target cell possesses a specific mechanism for converting the procytotoxin into a cytotoxin. The activated cytotoxic peptide acts on and destroys the target cell in a selective manner. Most conveniently, this cell-associated activity is a protease.

According to a preferred embodiment, a target cell contains a glutamate carboxypeptidase which cleaves gamma glutamate peptide bonds. When a γ-glutamate-masked cytolytic peptide is contacted with the target cell, the γ-glutamate residues are removed from the protoxin, and the resultant cytolytic peptide molecule causes lysis of the target cell. A non-target cell, which does not contain the glutamate carboxypeptidase, is unable to activate the protoxin and is thus unaffected by the protoxin.

A skilled person would readily recognize that if the glutamate residue is linked to the ε-amino group of a lysine, a carboxypeptidase, including the prostate specific membrane antigen discussed below, would be able to cleave the γ-linked glutamate residues regardless whether they are located at the C-terminus or the N-terminus of the cytotoxic peptide or somewhere in between.

Thus, it will be recognized that such an approach has broader applicability to cells associated with a particular activity that can be invoked to convert the protoxin to its toxin form. For example, when the target cell is associated with a chymotrypsin-like activity, the protoxin can be rendered non-toxic by modification with phenylalanine, tyrosine or tryptophan. Since these enzymes, and indeed serine proteases generally, are known to cleave C-terminally, relative to the amino acid target site, when phenylalanine, for example, is linked via an [ε-α] bond to lysine, the protease will cleave after the alpha carbonyl of phenylalanine, restoring the epsilon amino group of lysine (and the carboxy group of phenylalanine), thereby activating the toxin. Again, when the target cell has trypsin-like activity, the protoxin may be modified with a positively charged amino acid like lysine or arginine.

In cases where the target cell has a protease activity that is the same or similar to conventional proteases, like chymotrypsin and trypsin, there should not be unwanted activation of the protoxin. That is, normally, chymotrypsin and trypsin are localized primarily in the intracellular environment, which is not accessible to the present protoxin medicaments. In the case of disorders where the target cells are associated with elevated levels of outer membrane-associated proteases, which are contacted with the protoxin due to their extracellular location, only the diseased cells will have the capability of activating the protoxin to its toxic form. Accordingly, the present protoxins are envisioned as having low levels of toxicity.

The present invention also comprehends a method for the treatment of cancers. According to an embodiment of the present invention, a pharmaceutical composition comprising the inventive protoxin is administered to a cancer patient, whose cancer cells are target cells possessing, for example, the requisite glutamate carboxypeptidase (or other enzyme for pro-drug conversion) for activating the procytotoxin.

Therapeutic treatment of cancer using the instant cytolytic peptide-based procytotoxin is particularly advantageous because cytolytic peptides are known to be absorbed into the target cell membrane. Even after the target cell is lysed, therefore, the cytolytic peptides are prevented from acting on, and causing undesired destruction of, adjacent non-target cells. For example, see Leippe et al. (1991) Proc. Natl. Acad. Sci. 88: 7659-7663). Moreover, at least in the case where no extra stabilization steps (described above) are taken, it is noted that the instant medicaments are small peptides, which generally will have a fairly short half-life. Hence, even if small amounts of activated cytolytic peptide escapes the surface of the cancer cell, it should be reasonably short-lived and cause little, if any, destruction of non-target cells.

Particularly preferred embodiments of the present invention entail using γ-glutamate-masked amoebapore or γ-glutamate-masked melittin analogs to treat prostate cancer. It has been recently discovered that prostate cancer cells over-express a type II transmembrane protein, the prostate specific membrane antigen ("PSMA"). PSMA has an intracellular epitope that is immunoreactive toward the 7E11C5 immunoglobulin G monoclonal antibody. Horosczewicz et al. (1983), LNCAP model of human prostatic carcinoma, Cancer Res. 43: 1809-1818. In prostate cancer patients, PSMA is highly expressed on malignant prostate epithelia, but only marginally on normal prostate glands, and to a lesser degree on benign prostatic hypertrophic epithelia. Pinto et al. (1999) Prostate specific membrane antigen, a unique glutamate carboxypeptidase: a review of recent findings, *The Prostate J.* 1: 15-26; Wright et al. (1995) Expression of Prostate Specific Membrane Antigen (PSMA) in normal benign and malignant prostate tissues, *Urol. Oncol.* 1: 18-28; Lopes et al., (1990) Immunohistochemical and pharmacokinetic characterization of the site-specific immunoconjugate CYT-356 derived from antiprostate monoclonal antibody 7E11-C5, *Cancer Res.* 50: 623-6428; Troyer et al., Detection and characterization of the prostate-specific membrane antigen (PSMA) in tissue extracts and body fluids, *Int. J. Cancer* 62: 552-558.

The proteolytic domain of PSMA is located on the outside of the cell surface. Upon reaching the target cell, the procytotoxins of the invention, without having to be internalized by the target cell, will have their γ-glutamate residue(s) cleaved and removed, thereby they will be activated. The procytotoxins thus are activated precisely at the desired site of action, the target cell. This direct effect on the target cell increases the effectiveness of the prostate cancer cell killing. The activated cytolytic peptide immediately inserts into the target cell, leaving it almost no chance of acting upon adjacent, non-target cells. (In fact, it is possible that one end of the peptide is already inserted into the membrane before it is activated by PSMA.) Furthermore, as discussed above, the activated toxin is neutralized by the membrane therefore after the lysis of the target cell, the cytolytic peptides remain adsorbed in the membrane debris of the target cell and do not leak and harm non-target cells.

The inventors recently have recognized that a range of cancer cells, beyond those of prostate specificity, apparently have the ability to cleave the subject γ-glutamate-masked cytolytic peptides. (See Examples.) On the other hand, normal cells appear to lack this ability, rendering the inventive compounds highly effective in ablating cancer cells, yet leaving normal cells unaffected. Cancer cell types showing sensitivity to the inventive toxins include prostate, ovary, lung and melanoma. A search of public expressed sequence tag databases for PSMA-like molecules indicated that, whereas a number of cancers cells express proteins with significant degrees of homology to PSMA, normal cells do not. This observation likely explains the ability of the inventive molecules to act on a variety of tumor cells, while leaving normal cells unaffected.

In a further embodiment, the procytotoxin is maintained in inactive form by modification with a bulky hydrophobic amino acid, like phenylalanine, tyrosine and tryptophan, or positively charged amino acids, like lysine and arginine. Such protoxins are useful in treating target cells that are associated with a chymotrypsin- or trypsin-like activity. The artisan will be aware of other examples as well.

Target cells capable of activating such a toxin include pancreatic cancer cells, which are associated with elevated levels of TMPRSS3, a transmembrane serine protease. Walltrapp et al., Cancer Res. 60: 2602-06 (2000).

Optimal delivery routes, dosages and regimens for a given mammalian host can be readily ascertained by one skilled in the art. It will, of course, be appreciated that the actual dose used will vary according to the particular composition formulated, the particular compound used, the mode of application and the particular site, host and disease being treated. Many factors that modify the action of the drug will be taken into account including age, weight, sex, diet, time of administration, route of administration, rate of excretion, condition of the patient, drug combinations, reaction sensitivities and severity of the disease.

The following non-limiting examples are given by way of illustration only and are not to be considered limitations of this invention, and there are many apparent variations within the scope of this invention. The examples illustrate the in vitro activity of the compounds of this invention and are illustrative of the studies that the art has relied on for close to half a century as reasonably predictive of the efficacy of cancer chemotherapeutic compounds.

EXAMPLES

Example 1

Preparation of γ-Glutamate-masked Amoebapore Analog

The twenty-five amino acid, C-terminal amidated, amoebapore cytolytic peptide was synthesized by standard solid phase peptide synthesis, except that the ε amino group of the C-terminal lysine was blocked with a different blocking group from that used to block the ε-amino groups of the other two lysine residues in the peptide, so that the terminal ε block could be selectively removed. After selective removal of the blocking group from C-terminal lysine ε amino group, this amino group was linked to the γ carboxyl group of a first glutamate residue with blocked α amino and carboxyl groups by solution phase synthesis. This results in the addition of a γ glutamate linked side-chain glutamic acid residue.

The α amino group of this first glutamic acid residue was de-protected and a second glutamate residue was then linked to the de-protected a amino group via a γ glutamate linkage between the γ carboxyl group of the second glutamic acid residue and the a amino group of the first γ glutamate linked side-chain glutamic acid residue. The second γ glutamate linked side-chain glutamic acid residue was also added by solution phase chemistry. If desired, further γ glutamate linked side-chain glutamic acid residues may be added in the same fashion.

Below is shown a diagram of the initial cytolytic peptide and the procytolytic peptide synthesized by the addition of the two γ glutamate linked side-chain glutamic acid residue to the ε amino group of the C-terminal lysine.

Cytolytic Peptide:

N-Gly-Phe-Ile-Ala-Thr-Leu-Cys-Thr-Lys-Val-Leu-Asp-Phe-Gly-Ile-Asp-Lys-Leu-Ile-Gln-Leu-Ile-Glu-Asp-Lys-CONH$_2$

Procytolytic Peptide:

Example 2

Assay for the Cytolytic Activity of the Pore-forming Toxins

For cell lysis assay, $10^6$ LNCaP prostate tumor cells were cultured in 48-well plate in 200 µl culture medium containing different concentrations of the peptide. The culture medium for LNCaP cell was RPMI 1640 medium with 2 mM L-glutamine adjusted to contain 1.5 g/L sodium bicarbonate, 4.5 g/L glucose, 10 mM HEPES, 1.0 mM sodium pyruvate, 90%; fetal bovine serum 10%. The cells were treated with peptide in a $CO_2$ incubator for one hour.

Figure 1:
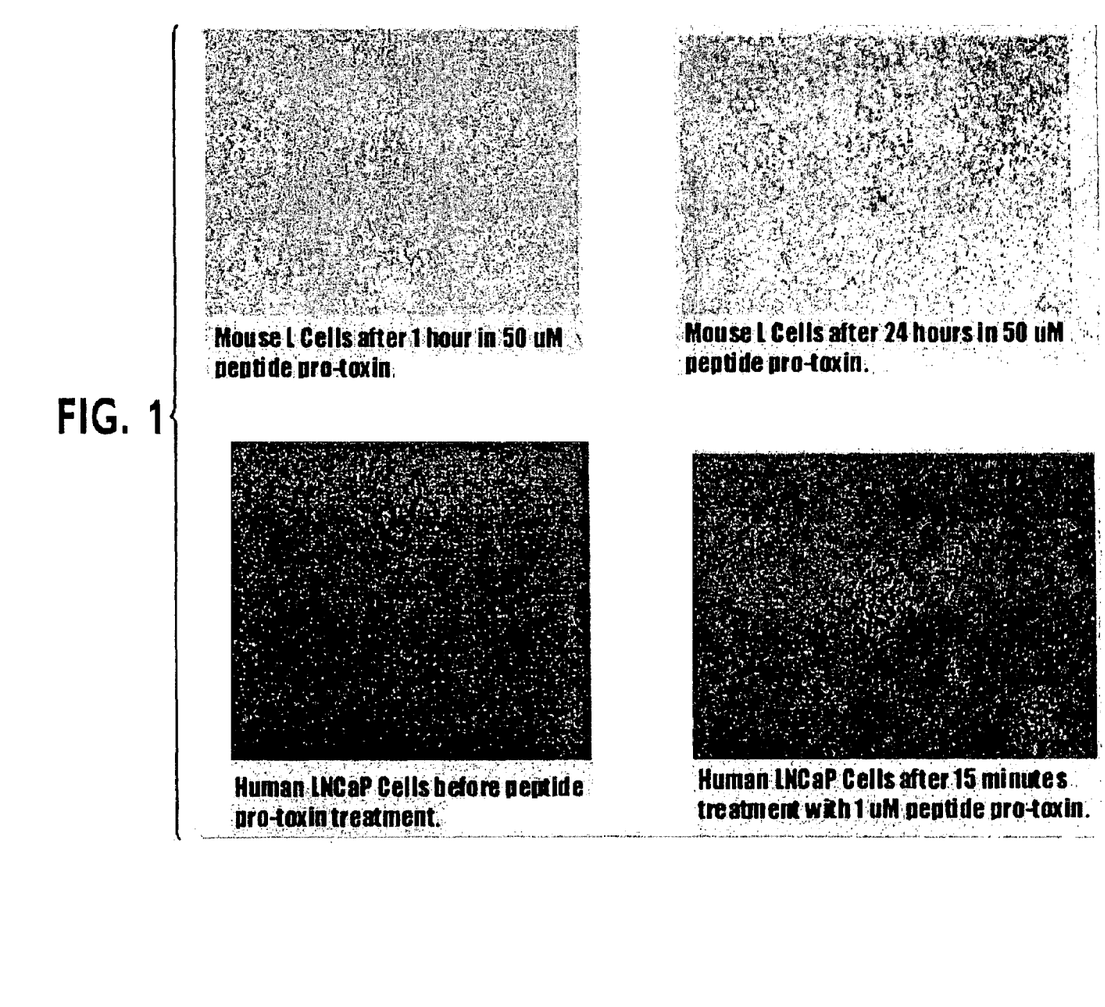
FIG. 1 shows that human prostate cancer cells (LNCaP) are completely lysed after 15 minutes in 50 μM amoebapore helix 3-γ-Glu-γ-Glu, while mouse L-cells remain unaffected after 24 hours under the same conditions.
Figure 2:
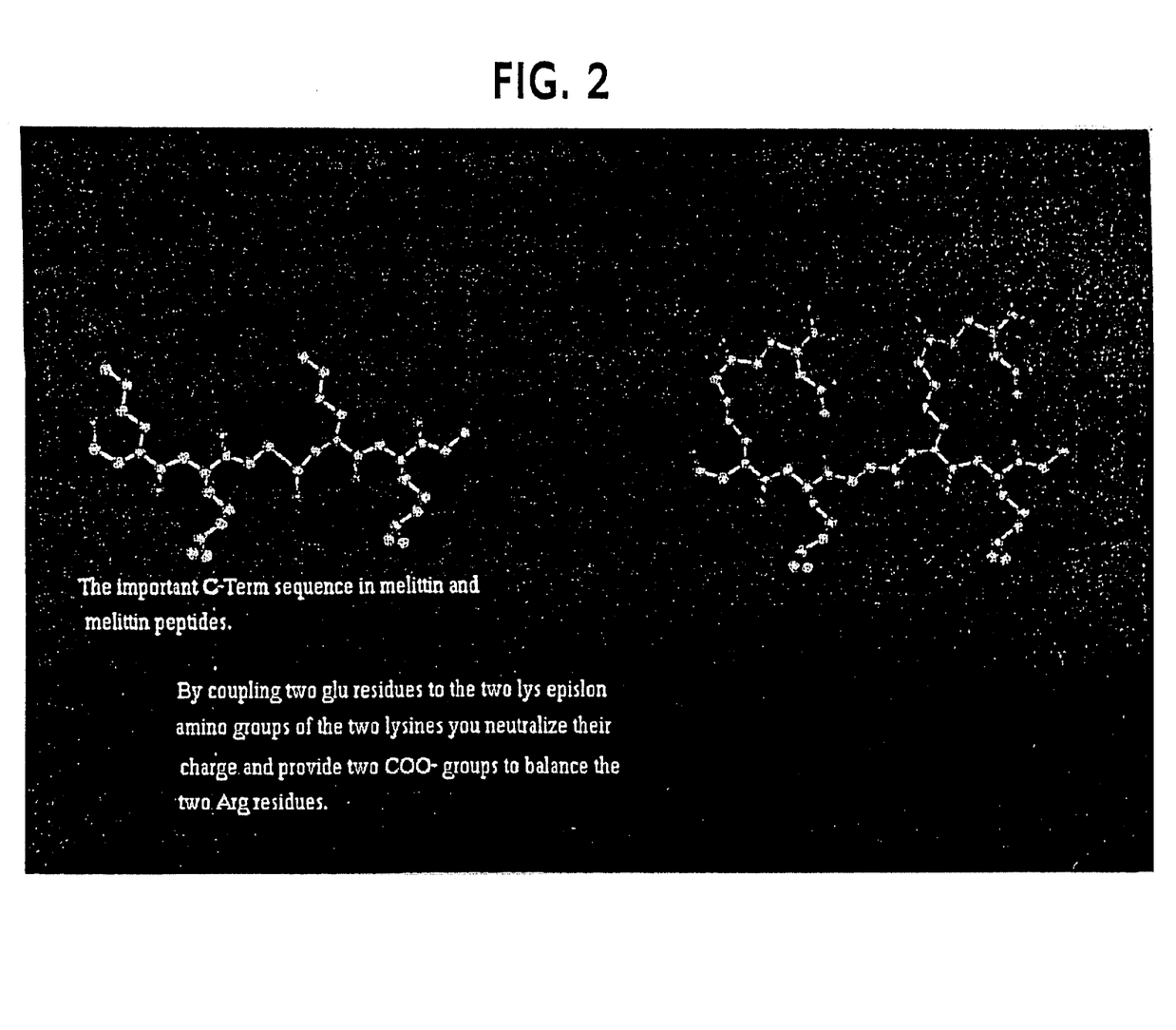
FIG. 2 shows the C-terminal sequences of melittin and melittin-like peptides (left) and illustrates that the ε-amino groups of the two lysines are coupled with two glutamate residues to neutralize the positive charges of the terminus (right).

As seen in FIG. 1, human prostate cancer cells (LNCaP) are completely lysed after 15 minutes in 50 μM amoebapore helix 3-γ-Glu-γ-Glu, while mouse L-cells remain unaffected after 24 hours under the same conditions.

In order to obtain a more quantitative result, the assay was repeated and decrease in ATP levels was used as a surrogate marker for live versus dead cells. ATP plays a central role in the energy status of the cell and the regulation of enzymatic activity. The intracellular ATP level is strictly regulated. The assay of ATP has been used as a rapid and convenient measure of viable cell numbers. ATP level can be enzymatically determined with firefly luciferase, which specifically catalyzes the hydrolysis of ATP. The amount of light generated by this enzymatic reaction is directly related to the amount of ATP in the original sample.

Figure 3:
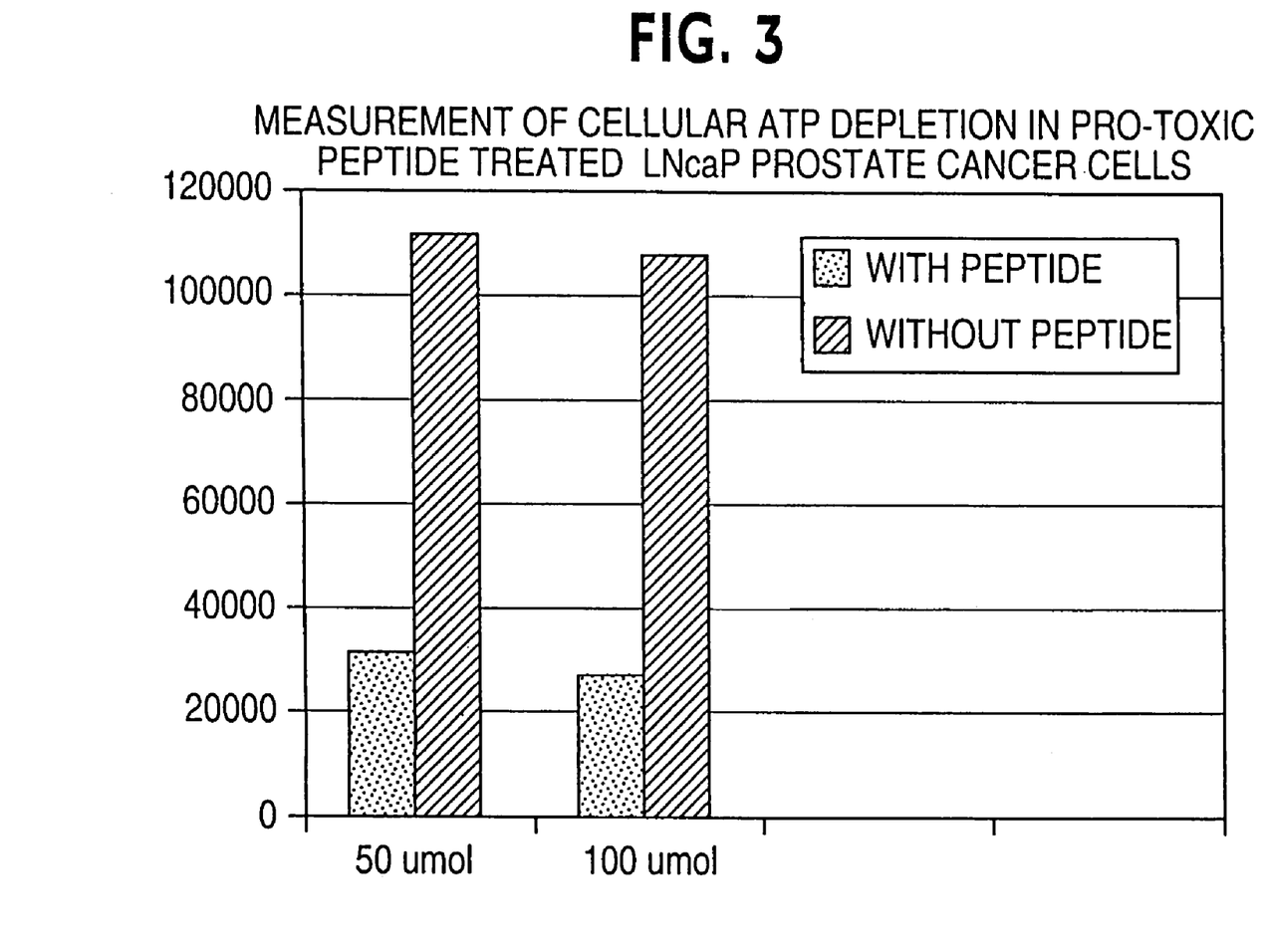
FIG. 3 demonstrates using an ATP depletion assay that human prostate cancer cells (LNCaP) are completely lysed after 1 hour in 50 or 100 µM amoebapore helix 3-γ-Glu-γ-Glu, while mouse L-cells remain unaffected.

For this purpose, the ATP Bioluminescence Assay Kit CLS II from Boehringer-Mannheim (Cat. No. 1699695) was employed. Briefly, $10^6$ cells in 200 μl of medium containing the peptide, as above, were incubated at 37° C. in a $CO_2$ incubator for 60 min. The cells were then lysed with 10 μl of 10% Triton X-100. Each lysate was transferred into a tube containing 155 μl of distilled water and 25 μl of stock luciferase and chemiluminescence was measured in a luminometer as directed by the mnaufacturer. As can been seen from FIG. 3, ATP is dramatically depleted in the presence of either 50 or 100 μM peptide, as compared to the controls.

Example 3

Specificity for Additional Tumor Types and Lack of Toxicity

Figure 4:
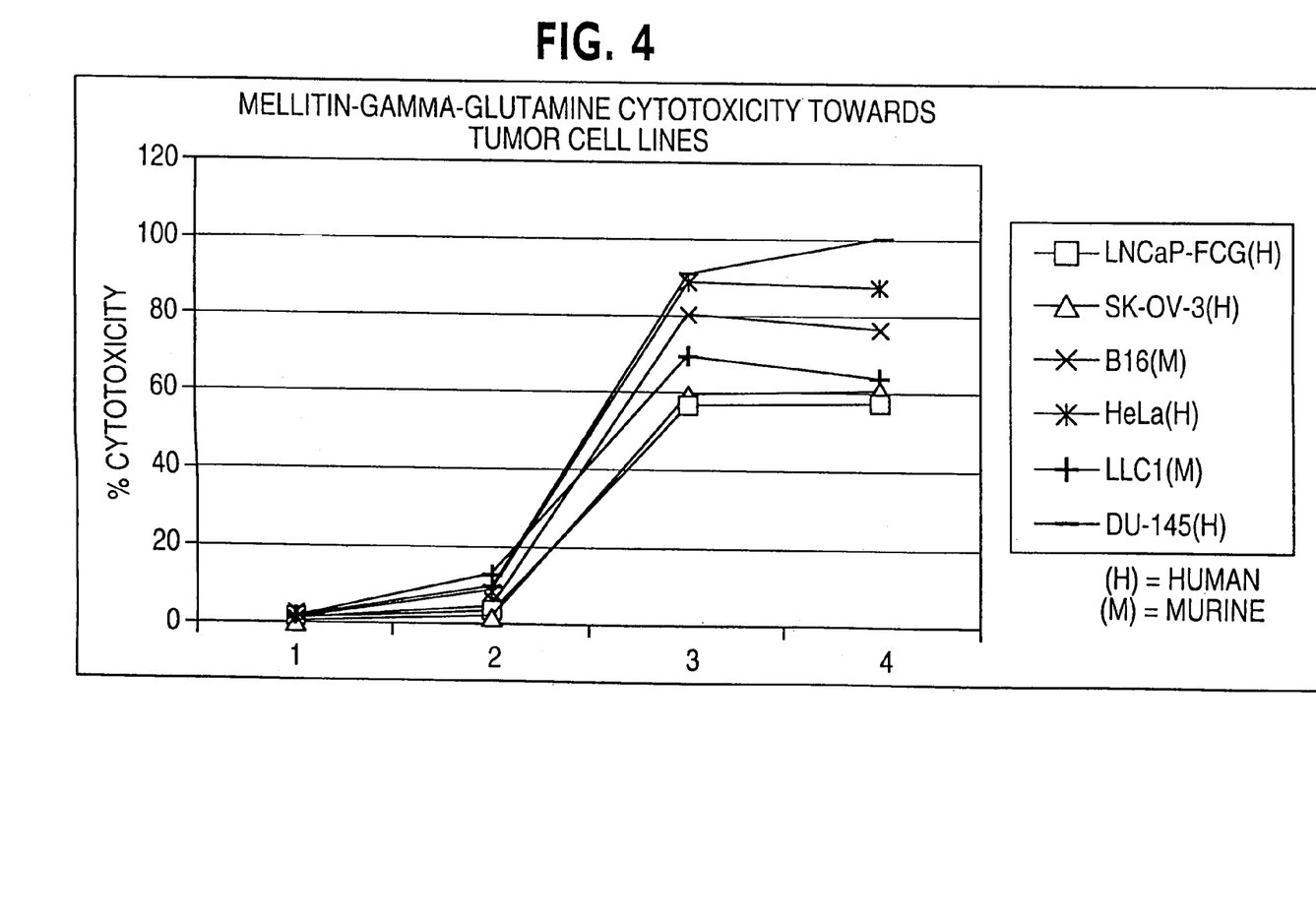
FIG. 4 shows dose responses of various tumors in vitro to an inventive masked melittin analog. The numbers 1, 2, 3 and 4 represent 1, 10, 50 and 100 µM analog, respectively.

This example demonstrates that the inventive γ-glutamate-masked cytolytic peptides have specificity for cancer cells other than those expressing PSMA. This experiment, utilized a melittin analog having A [ε-γ]-Glu-[α-γ]-Glu at each of lysines 21 and 23: $NH_2$-Gly-Ile-Gly-Ala-Val-Leu-Lys-Val-Leu-Thr-Thr-Gly-Leu-Pro-Ala-Leu-Ile-Ser-Trp-Ile-Lys([ε-γ]-Glu-[α-γ]-Glu)-Arg-Lys([ε-γ]-Glu-[(α-γ)-Glu)-Arg-Gln-Gln-COOH. Two prostate tumors (PNCap and DU0145), two ovarian tumors (HeLa and SK-OV-3), one lung tumor (LLC1) and one melanoma (B16) were tested. Cultured cells were treated with 1, 10, 50 or 100 μM peptide. Results, depicted in FIG. 4, show stron lytic activity against all tumors.

Figure 5:
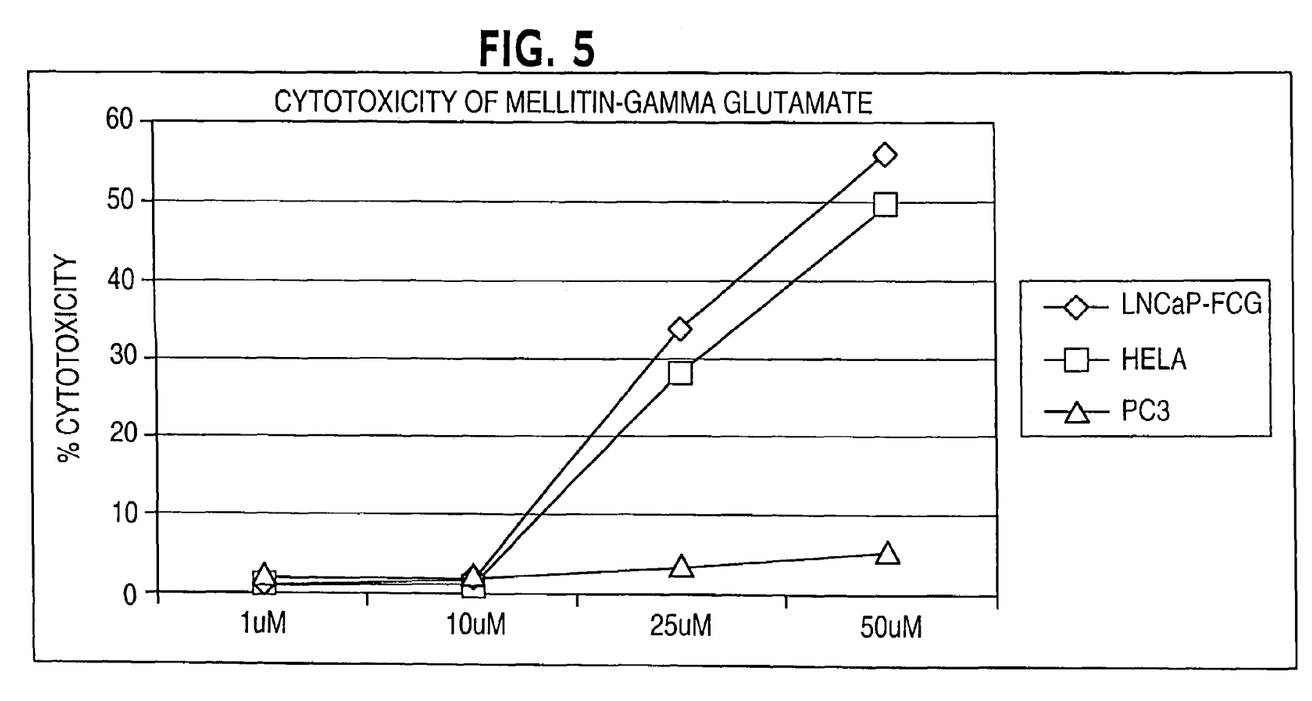
FIG. 5 shows that an inventive melittin analog selectively lyses PSMA-expressing and cancer cells, but does not lyse cells that do not express PSMA or a similar molecule.

The same analog was used to treat a PSMA-expressing prostate cells (LNCaP-FCG), ovarian cancer cells (HeLa) or prostate cells not expressing PSMA (PC3). While 25 and 50 mM concentrations were highly toxic to the PSMA-expressing prostate cells and the ovarian cancer cells, the non-PSMA-expressing prostate cells were relatively unaffected. See FIG. 5.

To assess the toxicity of this analog, mice were treated with escalating doses of analog, either subcutaneously or intravenously. At 50, 100, 150 and 200 mM concentrations (50-200-fold higher concentrations needed to kill a mouse using the unmasked mellitin peptide) mice remained healthy, apparently unaffected, for weeks following treatment. These data indicate that the subject peptides should be safe and effective in treating a variety of tumors.

What is claimed is:

1. A procytotoxin comprising a dimeric peptide, wherein:
   (a) a monomeric form of the dimeric peptide is modified to comprise at least one lysine residue bound via a peptide bond to at least one amino acid via the C-amino group of the lysine residue,
   (b) the monomeric form of the dimeric peptide without the modification is a pore-forming cytolytic peptide, and
   (c) the modification acts to prevent the peptide from forming a lyrically active conformation.

2. The procytotoxin of claim 1, wherein the pore-forming cytolytic peptide is selected from the group consisting of Ae I, cytolysin of sea anemone, aerolysin, amatoxin, amoebapore, amoebapore homolog from *Entamoeba dispar*, brevinin-1E, brevinin-2E, barbatolysin, cytolysin of *Enterococcus faecalis*, delta hemolysin, diphtheria toxin, El Tor cytolysin of *Vibrio cholerae*, equinatoxin, enterotoxin of *Aeromonas hydrophila*, esculentin, granulysin, haemolysin of *Vibrio parahaemolyticus*, intermedilysin of *Streptococcus intermedius*, the lentivirus lytic peptide, leukotoxin of *Actinobacillus actinomycetemcomitans*, magainin, melittin, membrane-associated lymphotoxin, Met-enkephalin, neokyotorphin, neokyotorphin fragment 1, neokyotorphin fragment 2, neokyotorphin fragment 3, neokyotorphin fragment 4, NK-lysin, paradaxin, perform perfringolysin O, theta-toxin, of *Clostridium perfringens*, phallolysin, phallotoxin, and streptolysin.

3. The procytotoxin of claim 2, wherein the cytolytic peptide is an amoebapore.

4. The procytotoxin of claim 3, wherein the monomeric form of the dimeric peptide comprises the following structure: Gly-Phe-Ile-Ala-Thr-Leu-Cys-Thr-Lys(R)-Val-Leu-Asp-Phe-Gly-Ile-Asp-Lys(R)-Leu-Ile-Gln-Leu-Ile-Glu-Asp-Lys(R) SEQ ID NO:1, wherein at least one (R) is independently selected from the group consisting of [ε-γ]-Glu, [ε-γ]-Glu-[α-γ]-(Glu)$_{1-3}$, [ε-α]-(Phe)$_{1-3}$, [ε-α]-(Tyr)$_{1-3}$, [ε-α]-(Trp)$_{1-3}$, [ε-α]-(Lys)$_{1-3}$ and [ε-α]-(Arg)$_{1-3}$, where:
   (a) [ε-γ] represents a peptide bond between the epsilon amino group of lysine and the gamma carboxyl group of the adjacent glutamate,
   (b) [ε-γ] represents a peptide bond between the alpha amino group of the first glutamate and the gamma carboxyl group of the second glutamate,
   (c) [ε-α] represents a peptide bond between the epsilon amino acid of lysine and the alpha carboxyl group of the indicated amino acid, and
   (d) the subscript indicates that additional numbers of the designated amino acid can be linked to the first via conventional peptide bonds.

5. The procytotoxin of claim 2, wherein the cytolytic peptide is a melittin.

6. The procytotoxin of claim 5, wherein the monomeric form of the dimeric peptide comprises the following structure: Gly-Ile-Gly-Ala-Val-Leu-Lys(R)-Val -Leu-Thr-Thr-Gly-Leu-Pro-Ala-Leu-Ile-Ser-Trp-Lle-Lys(R)-Arg-Lys(R)-Arg-Gln-Gln SEQ ID NO:2, wherein at least one (R) is independently selected from the group consisting of [ε-γ]-Glu, [ε-γ]-Glu-[α-γ]-(Glu)$_{1-3}$, [ε-α]-(Phe)$_{1-3}$, [ε-α]-(Tyr)$_{1-3}$, [ε-α]-(Trp)$_{1-3}$, [ε-α]-(Lys)$_{1-3}$ and [ε-α]-(Arg)$_{1-3}$, wherein:
   (a) [ε-γ] represents a peptide bond between the epsilon amino group of lysine and the gamma carboxyl group of the adjacent glutamate,
   (b) [α-γ] represents a peptide bond between the alpha amino group of the first glutamate and the gamma carboxyl group of the second glutamate,
   (c) [ε-α] represents a peptide bond between the epsilon amino acid of lysine and the alpha carboxyl group of the indicated amino acid, and
   (d) the subscript indicates that additional numbers of the designated amino acid can be linked to the first via conventional peptide bonds.

7. A procytotoxin comprising a dimeric peptide, wherein a monomeric form of the dimeric peptide comprises the structure selected from the group consisting of: N-Gly-Phe-Ile-Ala-Thr-Leu-Cys-Thr-Lys-Val-Leu-Asp-Phe-Gly-Ile-Asp-Lys-Leu-Ile-Gln-Leu-Ile-Glu-Asp-Lys([ε-γ]-Glu-[α-γ]-Glu)-CONH$_2$ SEQ ID NO:8 and NH$_2$-Gly-Ile-Gly-Ala-Val-Leu-Lys-Val-Leu-Thr-Thr-Gly-Leu-Pro-Ala-Leu-Ile-Ser-Trp-Ile-Lys([ε-γ]-Glu-[α-γ]-Glu)-Arg-Lys([-γ]-Glu-[α-γ]-Glu)-Arg-Gln-Gln-COOH SEQ ID NO:12.

8. A pharmaceutical composition, comprising the procytotoxin of claim 1, and a pharmaceutically acceptable excipient.

9. A method for selectively destroying a target cell, comprising contacting the target cell with the procytotoxin of claim 1, wherein the target cell is a cancer cell.

10. The method of claim 9, wherein the cancer cell is selected from the group consisting of a prostate cell, an ovarian cell, a lung cell and a skin cell.

11. The method of claim 9, wherein the cytolytic peptide is an amoebapore.

12. A method for selectively destroying a target cell, comprising contacting the target cell with the procytotoxin of claim 4, wherein the target cell is a cancer cell.

13. The method of claim 9, wherein the cytolytic peptide is a melittin.

14. A method for selectively destroying a target cell, comprising contacting the target cell with the procytotoxin of claim 6, wherein the target cell is a cancer cell.

15. A method for selectively destroying a target cell, comprising contacting the target cell with the procytotoxin of claim 7, wherein the target cell is a cancer cell.

* * * * *

SEQUENCE LISTING

```
<160> NUMBER OF SEQ ID NOS: 12

<210> SEQ ID NO 1
<211> LENGTH: 37
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(13)
<223> OTHER INFORMATION: This region may be selected from the group
      consisting of [epsilon-gamma]-Glu, [epsilon-gamma]-Glu-[alpha-
      gamma]-(Glu)1-3, [epsilon-alpha]-(Phe)1-3, [epsilon-alpha]-
      (Tyr)1-3, [epsilon-alpha]-(Trp)1-3, [epsilon-alpha]-(Lys)1-3 and
      [epsilon-alpha]-(Arg)1-3.
<220> FEATURE:
<221> NAME/KEY: MOD_RES
<222> LOCATION: (22)..(25)
<223> OTHER INFORMATION: This region may be selected from the group
      consisting of [epsilon-gamma]-Glu, [epsilon-gamma]-Glu-[alpha-
      gamma]-(Glu)1-3, [epsilon-alpha]-(Phe)1-3, [epsilon-alpha]-
      (Tyr)1-3, [epsilon-alpha]-(Trp)1-3, [epsilon-alpha]-(Lys)1-3 and
      [epsilon-alpha]-(Arg)1-3.
<220> FEATURE:
<221> NAME/KEY: MOD_RES
<222> LOCATION: (34)..(37)
<223> OTHER INFORMATION: This region may be selected from the group
      consisting of [epsilon-gamma]-Glu, [epsilon-gamma]-Glu-[alpha-
      gamma]-(Glu)1-3, [epsilon-alpha]-(Phe)1-3, [epsilon-alpha]-
      (Tyr)1-3, [epsilon-alpha]-(Trp)1-3, [epsilon-alpha]-(Lys)1-3 and
      [epsilon-alpha]-(Arg)1-3.
<220> FEATURE:
<223> OTHER INFORMATION: This molecule may encompass smaller embodiments
``` according to the application as filed

<400> SEQUENCE: 1

Gly Phe Ile Ala Thr Leu Cys Thr Lys Xaa Xaa Xaa Xaa Val Leu Asp
1               5                   10                  15

Phe Gly Ile Asp Lys Xaa Xaa Xaa Xaa Leu Ile Gln Leu Ile Glu Asp
            20                  25                  30

Lys Xaa Xaa Xaa Xaa
        35

<210> SEQ ID NO 2
<211> LENGTH: 38
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(11)
<223> OTHER INFORMATION: This region may be selected from the group
      consisting of [epsilon-gamma]-Glu, [epsilon-gamma]-Glu-[alpha-
      gamma]-(Glu)1-3, [epsilon-alpha]-(Phe)1-3, [epsilon-alpha]-
      (Tyr)1-3, [epsilon-alpha]-(Trp)1-3, [epsilon-alpha]-(Lys)1-3 and
      [epsilon-alpha]-(Arg)1-3.
<220> FEATURE:
<221> NAME/KEY: MOD_RES
<222> LOCATION: (26)..(29)
<223> OTHER INFORMATION: This region may be selected from the group
      consisting of [epsilon-gamma]-Glu, [epsilon-gamma]-Glu-[alpha-
      gamma]-(Glu)1-3, [epsilon-alpha]-(Phe)1-3, [epsilon-alpha]-
      (Tyr)1-3, [epsilon-alpha]-(Trp)1-3, [epsilon-alpha]-(Lys)1-3 and
      [epsilon-alpha]-(Arg)1-3.
<220> FEATURE:
<221> NAME/KEY: MOD_RES
<222> LOCATION: (32)..(35)
<223> OTHER INFORMATION: This region may be selected from the group
      consisting of [epsilon-gamma]-Glu, [epsilon-gamma]-Glu-[alpha-
      gamma]-(Glu)1-3, [epsilon-alpha]-(Phe)1-3, [epsilon-alpha]-
      (Tyr)1-3, [epsilon-alpha]-(Trp)1-3, [epsilon-alpha]-(Lys)1-3 and
      [epsilon-alpha]-(Arg)1-3.
<220> FEATURE:
<223> OTHER INFORMATION: This molecule may encompass smaller embodiments
      according to the application as filed

<400> SEQUENCE: 2

Gly Ile Gly Ala Val Leu Lys Xaa Xaa Xaa Xaa Val Leu Thr Thr Gly
1               5                   10                  15

Leu Pro Ala Leu Ile Ser Trp Ile Lys Xaa Xaa Xaa Xaa Arg Lys Xaa
            20                  25                  30

Xaa Xaa Xaa Arg Gln Gln
        35

<210> SEQ ID NO 3
<211> LENGTH: 25
<212> TYPE: PRT
<213> ORGANISM: Entamoeba histolytica

<400> SEQUENCE: 3

Gly Phe Ile Ala Thr Leu Cys Thr Lys Val Leu Asp Phe Gly Ile Asp
1               5                   10                  15

Lys Leu Ile Gln Leu Ile Glu Asp Lys
            20                  25

<210> SEQ ID NO 4
<211> LENGTH: 37
<212> TYPE: PRT
<213> ORGANISM: Antheraea pernyi

```
<220> FEATURE:
<223> OTHER INFORMATION: Cecropin A

<400> SEQUENCE: 4

Lys Trp Lys Leu Phe Lys Lys Ile Glu Lys Val Gly Gln Asn Ile Arg
 1               5                  10                  15

Asp Gly Ile Ile Lys Ala Gly Pro Ala Val Ala Val Val Gly Gln Ala
            20                  25                  30

Thr Gln Ile Ala Lys
        35

<210> SEQ ID NO 5
<211> LENGTH: 35
<212> TYPE: PRT
<213> ORGANISM: Antheraea pernyi
<220> FEATURE:
<223> OTHER INFORMATION: Cecropin B

<400> SEQUENCE: 5

Lys Trp Lys Ile Phe Lys Lys Ile Glu Lys Val Gly Arg Asn Ile Arg
 1               5                  10                  15

Asn Gly Ile Ile Lys Ala Gly Pro Ala Val Ala Val Leu Gly Glu Ala
            20                  25                  30

Lys Ala Leu
        35

<210> SEQ ID NO 6
<211> LENGTH: 36
<212> TYPE: PRT
<213> ORGANISM: Antheraea pernyi
<220> FEATURE:
<223> OTHER INFORMATION: Cecropin D

<400> SEQUENCE: 6

Trp Asn Pro Phe Lys Glu Leu Glu Lys Val Gly Gln Arg Val Arg Asp
 1               5                  10                  15

Ala Val Ile Ser Ala Gly Pro Ala Val Ala Thr Val Ala Gln Ala Thr
            20                  25                  30

Ala Leu Ala Lys
        35

<210> SEQ ID NO 7
<211> LENGTH: 26
<212> TYPE: PRT
<213> ORGANISM: Apis mellifera

<400> SEQUENCE: 7

Gly Ile Gly Ala Val Leu Lys Val Leu Thr Thr Gly Leu Pro Ala Leu
 1               5                  10                  15

Ile Ser Trp Ile Lys Arg Lys Arg Gln Gln
            20                  25

<210> SEQ ID NO 8
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (26)..(27)
<223> OTHER INFORMATION: [epsilon-gamma]-Glu-[alpha-gamma]-Glu
```

```
<400> SEQUENCE: 8

Gly Phe Ile Ala Thr Leu Cys Thr Lys Val Leu Asp Phe Gly Ile Asp
  1               5                  10                  15

Lys Leu Ile Gln Leu Ile Glu Asp Lys Xaa Xaa
             20                  25

<210> SEQ ID NO 9
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (26)
<223> OTHER INFORMATION: [epsilon-alpha]-Phe

<400> SEQUENCE: 9

Gly Phe Ile Ala Thr Leu Cys Thr Lys Val Leu Asp Phe Gly Ile Asp
  1               5                  10                  15

Lys Leu Ile Gln Leu Ile Glu Asp Lys Xaa
             20                  25

<210> SEQ ID NO 10
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (18)
<223> OTHER INFORMATION: [epsilon-alpha]-Phe
<220> FEATURE:
<221> NAME/KEY: MOD_RES
<222> LOCATION: (27)
<223> OTHER INFORMATION: [epsilon-alpha]-Phe

<400> SEQUENCE: 10

Gly Phe Ile Ala Thr Leu Cys Thr Lys Val Leu Asp Phe Gly Ile Asp
  1               5                  10                  15

Lys Xaa Leu Ile Gln Leu Ile Glu Asp Lys Xaa
             20                  25

<210> SEQ ID NO 11
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (22)
<223> OTHER INFORMATION: [epsilon-gamma]-Glu
<220> FEATURE:
<221> NAME/KEY: MOD_RES
<222> LOCATION: (25)
<223> OTHER INFORMATION: [epsilon-gamma]-Glu

<400> SEQUENCE: 11

Gly Ile Gly Ala Val Leu Lys Val Leu Thr Thr Gly Leu Pro Ala Leu
  1               5                  10                  15

Ile Ser Trp Ile Lys Xaa Arg Lys Xaa Arg Gln Gln
             20                  25
```

```
<210> SEQ ID NO 12
<211> LENGTH: 30
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (22)..(23)
<223> OTHER INFORMATION: [epsilon-gamma]-Glu-[alpha-gamma]-Glu
<220> FEATURE:
<221> NAME/KEY: MOD_RES
<222> LOCATION: (26)..(27)
<223> OTHER INFORMATION: [epsilon-gamma]-Glu-[alpha-gamma]-Glu

<400> SEQUENCE: 12

Gly Ile Gly Ala Val Leu Lys Val Leu Thr Thr Gly Leu Pro Ala Leu
 1               5                  10                  15

Ile Ser Trp Ile Lys Xaa Xaa Arg Lys Xaa Xaa Arg Gln Gln
                20                  25                  30
```